United States Patent [19]

Endo et al.

[11] Patent Number: 4,701,448
[45] Date of Patent: Oct. 20, 1987

[54] METAL SALT OF ORGANIC PHOSPHATE AND AN ANTIHYPERLIPEMIC AGENT CONTAINING THE SAME

[75] Inventors: Akira Endo, Tokyo; Haruyuki Yamashita, Urawa, both of Japan

[73] Assignee: Asahi Denka Kogyo Kabushiki Kaisha, Tokyo, Japan

[21] Appl. No.: 823,762

[22] Filed: Jan. 29, 1986

[30] Foreign Application Priority Data

Jan. 29, 1985 [JP] Japan ................... 60-15120

[51] Int. Cl.$^4$ ............... C07F 9/117; C07F 5/06
[52] U.S. Cl. .................. 514/121; 558/179; 514/492; 514/494; 514/499; 514/501; 514/502; 556/24; 556/174
[58] Field of Search .......... 556/24, 174; 558/179; 514/492, 121, 501, 502, 494, 499

[56] References Cited

U.S. PATENT DOCUMENTS 3,310,575  3/1967  Spivack .................. 556/174
3,723,578  3/1973  Eiseman, Jr. et al. ....... 556/24 X Primary Examiner—Helen M. S. Sneed
Attorney, Agent, or Firm—Young & Thompson

[57] ABSTRACT

A metal salt of an organic phosphate, having good stability and cholesterol-lowering activity, is produced by reacting a known compound

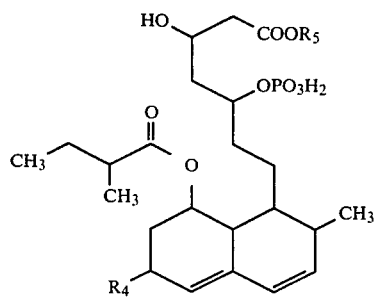

wherein $R_4$ and $R_5$ are hydrogen or methyl, with a reaction agent such as metal hydroxide.

4 Claims, No Drawings

METAL SALT OF ORGANIC PHOSPHATE AND AN ANTIHYPERLIPEMIC AGENT CONTAINING THE SAME

FIELD OF THE INVENTION

The present invention relates to a metal salt of organic phosphate and an antihyperlipemic agent containing the same as an active component.

DESCRIPTION OF PRIOR ARTS

The compound having the following general formula (2) is known in the art.

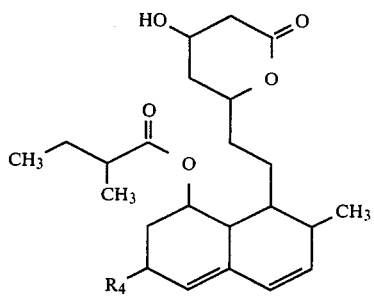
(2)

Monacolin K [$R_4$=$CH_3$ in the formula (2) U.S. Pat. No. 4,231,938] and ML-236B [$R_4$=H in the formula (2) U.S. Pat. No. 3,983,140] are produced from Monascus ruber and Penicillium citrinum, respectively.

It is also known that they inhibit the biosynthesis of cholesterol by an enzyme system or a cultured cell system separated from experimental animals by competing with its rate-limiting enzyme, 3-hydroxy-3-methylglutaryl coenzyme A reductase, and as the result they exhibit an excellent action of lowering serum cholesterol level of animals [Journal of Antibiotics, vol. 33, pp.334–336 (1980) and vol. 29, pp.1346–1348 (1976), as well as Japanese Patent Laid-Open No. 155690/1975].

The compound having the following general formula (3) is also known in the art.

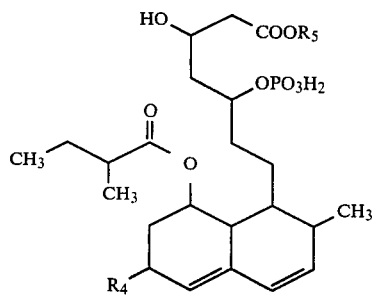
(3)

(Wherein $R_4$ is the same as defined above and $R_5$ is hydrogen atom or methyl)

CB3A [$R_4$=H, $R_5$=H in the formula (3)]. CB3A methyl ester [$R_4$=H, $R_5$=$CH_3$ in the formula (3)]. CK3A [$R_4$=$CH_3$, $R_5$=H in the formula (3)] and CK3A methyl ester [$R_4$=$CH_3$, $R_5$=$CH_3$ in the formula (3)] are substances which were produced by the present inventors by the conversion of ML-236B and monacolin K using a specific microorganism. The present inventors have found that these substances have a strong activity of inhibiting the synthesis of cholesterol (Japanese Patent Application No. 165490/1983, Journal of antibiotics, 38, pp 328–332 (1985)).

However CB3K, CK3A and their methyl esters represented by the formula (3) are unstable and unsatisfactory in its absorbability and effect.

SUMMARY OF THE INVENTION

As the extinsive studies on the hypocholesteremic effect, absorbability, long activity, pungency and the like of the compound of the formula (3), the present inventors have found that a metal salt of organic phosphate having the general formula (1) shown below has an unexpected property that is extremely stable and show an excellent cholesterol lowering action.

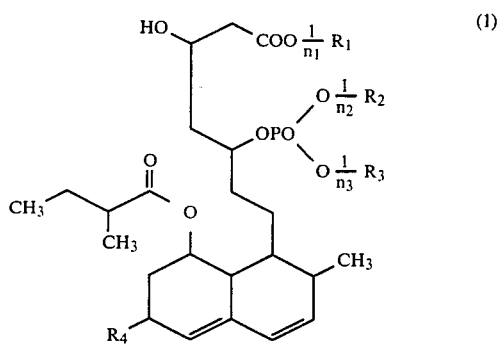
(1)

(wherein $R_1$, $R_2$ and $R_3$ are selected from the group consisting of hydrogen atom, alkyl group, alkali metal, alkaline earth metal, aluminum, iron, zinc, copper, nickel and cobalt, at least one of $R_1$, $R_2$ and $R_3$ being a metal; $n_1$, $n_2$ and $n_3$ are valences of $R_1$, $R_2$ and $R_3$, respectively; $R_4$ is hydrogen atom or methyl group; provided that there is excluded the case where $R_1$ is hydrogen or methyl group, and $R_2$ and $R_3$ are hydrogen atom.)

Based on this finding, they have completed the present invention.

Accordingly, the present invention provides a novel metal salt of organic phosphate represented by the formula (1). The present invention further provides an antihyperlipemic agent comprising the same as active component.

DESCRIPTION OF THE PREFERRED EMBODIMENTS

According to the present invention, as the metal represented as $R_1$, $R_2$ and $R_3$ in the formula (1), there are exemplified alkali metal such as sodium and potassium, alkaline earth metal such as calcium, magnesium and barium, as well as aluminum, iron, zinc, nickel and cobalt. Among these, alkali metal, alkaline earth metal and aluminum are preferable; alkaline earth metal and aluminum are more preferable; and calcium and aluminum are most preferable.

A metal salt of organic phosphate of the present invention is prodeced for example by reacting CB3A, CK3A or their alkyl ester directly with a hydroxide such as sodium, calcium or aluminum hydroxide or a chloride such as calcium chloride or by reacting an alkali metal salt of CB3A, CK3A or their alkyl ester with a metal salt such as calcium, barium or aluminum chloride.

The starting materials, CB3A and CK3A can be produced according to the process disclosed in Japanese Patent Application No. 165490/1983 which comprises letting Monacolin K or ML-236B interact with a microorganism belonging to the genus Absidia or the genus Circinella or an enzyme produced by the microorganism. A preferrable process comprises immobilizing spores of fungi of the genus Circinella or the genus Absidia on a salt-coagulated polysaccharide as a support to form a spore-immobilized product; germinating it to form a hypha plexus; separating it from the "growth" culture medium; and aerobically culturing it in a ML-236B- or Monacolin K - containing culture medium.

As an example of fungi of the genus Circinella used for the preparation of this fungi-immobilized product, there is mentioned *Circinella muscae* IFO (Institute for Fermentation, Osaka, Japan )6410, IFO 4457. As fungi of the genus Absidia there are mentioned for example *Absidia cylindrospora* IFO 4000 and *Absidia glauca* IFO 4003. These fungi are easily available from the Official Microorganism Depositories such as IFO.

The fungi-immobilized product is obtained by immobilizing spores of fungi. When mycelium is used, it is difficult to disperse it uniformly in an immobilized product. However when spores are used, uniform dispersing is possible and, when germinated in an immobilized product, they can form a uniform hypha plexus.

As the salt-coagulated polysaccharide used for the fungi-immobilized product, it is preferrable to use κ-carrageenan in view of gel strength and the growth of mycelium. Other substances such as pectin and alginic acid are usable conditionally. By immobilizing fungi with this salt-coagulated polysaccharide, there can be obtained a fungi immobilized product which is excellent in the growth of hypha after germination.

As a method of culturing fungi of the genus Circinella or the genus Absidia, aerobically culturing is essential. Therefore, it is necessary that a fungi-immobilized product has appropriate strength and is infragible. The preferrable shape thereof is a globular gel having a diameter of 0.5 to 10 mm, preferrably 1 to 4 mm.

The fungi-immobilized product is preferably produced by dispersing spores of the fungi of the genus Circinella or the genus Absidia in an aqueous solution of the salt-coagulated polysaccharide and thereafter dropping the aqueous solution of salt-coagulated polysaccharide into an immobilized liquid comprising an aqueous salt solution and a water-insoluble oil layered thereon to obtain a fungi-immobilized gel having an approximately globular form.

As methods for forming a gel using a salt-coagulated polysaccharide such as carrageenan, there are known a method of allowing to stand at low temperature, a method of contacting with an aqueous salt solution, etc.

However the former method requiring fine molds and considerable labors is not a preferable method.

In the latter method, spores of the fungi of the genus Circinella or the genus Absidia are dispersed in an aqueous solution of salt-coagulated polysaccharide, and the dispersion is dropped into an aqueous salt solution with a suitable means such as injector. Since the aqueous solution of salt-coagulated polysaccharide forms gel immediately after contacting with the aqueous salt solution, it coagulates distortedly because of an impact at its collision with the surface of the aqueous salt solution, and the formation of a fungi-immobilized product having a globular form is impossible. Therefore it is preferable to drop an aqueous solution of salt-coagulated polysaccharide into an immobilizing liquid in which a water insoluble oil is layered on an aqueous salt solution, because the polysaccharide solution becomes globular during its passing through the oil layer and then contacts with the aqueous salt solution to give a fungi-immobilized gel having an approximately globular form.

The aqueous solution of salt-coagulated polysaccharide used for the preparation of the fungi-immobilized product is an aqueous solution of salt-coagulated polysaccharide used as a carrier in the above mentioned fungi-immobilized product. An aqueous solution of κ-carrageenan is particularly preferred. The preferable concentration of the polysaccharide in the solution is from 0.5 to 5% by weight.

The number of spores dispersed in the aqueous polysaccharide solution is preferably from $10^2$ to $10^9$ /ml.

As the water-insoluble oil used, any substance can be used which is substantially immiscible with water and lighter than water. The preferable examples thereof are liquid paraffin, soy bean oil, rape(seed) oil, oleic acid, linoleic acid or the like.

A thickness of the water-insoluble oil layer in the immobilizing liquid is generally from 1 to 5 cm, although it may depend on a diameter of the immobilized gel desired and a specific gravity of the oil. A thickness exceeding 5 cm may be employed, but an additional effect can not be expected.

The aqueous salt solution by which the aqueous solution of salt-coagulated polysaccharide forms gel, is selected considering salt-coagulated polysaccharides actually used. For example, when an aqueous solution of κ-carrageenan is used as the aqueous solution of salt-coagulated polysaccharides, there can be used an aqueous solution of potassium chloride, calcium chloride, ammonium chloride, magnesium chloride or the like. An aqueous potassium chloride solution is preferable. A concentration of the salt in the solution is preferable from 0.05 to 0.3 mol/l.

The process for producing CB3A or CK3A using the above mentioned fungi-immobilized product comprises germinating spores in the fungi-immobilized product obtained above and using this to convert ML-236B or Monacolin K to CB3A ($R_4$=H) or CK3A ($R_4$=CH$_3$) represented by the above mentioned formula (3).

In order to germinate the fungi-immobilized product composed of a fungi-immobilized gel having an approximately globular form, a suitable amount, e.g. from 0.5 to 80% by weight of the immobilized product is added to a culture medium comprising a suitable nutrient sources, e.g. carbon sources such as glucose, glycerin, sucrose, maltose, citrates and soluble starch; nitrogen sources such as corn steep liquor, meat extract, yeast extract, polypeptone, urea and ammonium sulfate; and vitamines such as biotin and thiamine. Thereafter aerobically culturing is conducted for a few days at or around normal temperature, whereby spores are germinated to form hypha plexus.

The conversion of ML-236B or Monacolin K to CB3A or CK3A is effectively conducted by separating from a "growth" culture medium, the fungi-immobilized product of which spores were germinated to form a hypha plexus as mentioned above; adding the separated fungi-immobilized product to a "conversion" culture medium containing ML-236B or Monacolin K, other necessary components (e.g. metal salts of magnesium, iron or manganese, and energy source such as glucose) and a buffer solution (pH ca 6.0) of a salt such as potassium phosphate; and conducting aerobically culturing. It is preferable that the conversion culture medium is free from nitrogen source to avoid complexity of post-treatment. The amount of the fungi-immobilized product to the conversion culture medium is generally from 0.5 to 80% by weight.

Described below are the cholesterol lowering activity and toxicity of the metal salt of organic phosphate according to the present invention.

(1) Serum cholesterol lowering activity the metal salt of organic phosphate according to the present invention was orally administered to a rabbit (body weight of about 3 Kg) two times a day (at 9:00 a.m. and 4:00 p.m.) for 5 successive days. After 5 days, blood was sampled and the total cholesterol value in serum was measured in a conventional manner. The results are shown in Table 1.

It is clear that the compound of the present invention has excellent serum cholesterol lowering activity compared with CB3A and CK3A.

TABLE 1

Serum Cholesterol Lowering Activity Against A Rabbit

| Compound | Dose (mg/kg/day) | Total Serum cholesterol lowering rate (%) |
|---|---|---|
| CB3A-3Na salt | 1.5 | 18.5 |
| | 6 | 34.3 |
| CB3A-3K salt | 1.5 | 19.4 |
| | 6 | 33.9 |
| CB3A-2K salt | 1.5 | 19.1 |
| | 6 | 34.2 |
| CB3A-1K salt | 1.5 | 19.6 |
| | 6 | 33.7 |
| CB3A-1.5Ca salt | 1.5 | 23.2 |
| | 6 | 40.2 |
| CB3A-1.5Mg salt | 1.5 | 21.1 |
| | 6 | 36.3 |
| CB3A-1.5Ba salt | 1.5 | 21.3 |
| | 6 | 36.6 |
| CB3A-Al salt | 1.5 | 24.2 |
| | 6 | 41.6 |
| CB3A methyl ester-2K salt | 1.5 | 19.5 |
| | 6 | 33.8 |
| CB3A methyl ester-Ca salt | 1.5 | 23.0 |
| | 6 | 40.6 |
| CK3A-3Na salt | 1.5 | 17.1 |
| | 6 | 30.0 |
| CK3A-3K salt | 1.5 | 18.9 |
| | 6 | 34.7 |
| Ck3A-1.5Ca salt | 1.5 | 24.5 |
| | 6 | 39.9 |
| CK3A-1.5Mg salt | 1.5 | 22.1 |
| | 6 | 36.3 |
| CK3A-1.5Ba salt | 1.5 | 21.1 |
| | 6 | 36.6 |
| CK3A-Al salt | 1.5 | 23.4 |
| | 6 | 41.6 |
| CK3A methyl ester-2K salt | 1.5 | 18.7 |
| | 6 | 34.7 |
| CK3A methyl ester-Ca salt | 1.5 | 24.9 |
| | 6 | 39.2 |
| CB3A | 1.5 | 9.4 |
| | 6 | 23.9 |
| CK3A | 1.5 | 9.7 |
| | 6 | 24.4 |

(2) Acute toxicity

The acute toxicity of the metal salt of CB3A and of CK3A was examined by orally or peritoneally administrating an aqueous solution or dispersion thereof the results are shown in Table 2.

TABLE 2

| Compound | Animal | Administration route | $LD_{50}$ (mg/kg) |
|---|---|---|---|
| CB3A-3K salt | mouse | a | >2000 |
| | | b | >500 |

TABLE 2-continued

| Compound | Animal | Administration route | $LD_{50}$ (mg/kg) |
|---|---|---|---|
| | rat | a | >2000 |
| | | b | >500 |
| CB3A-3Na salt | mouse | a | >2000 |
| | | b | >500 |
| | rat | a | >2000 |
| | | b | >500 |
| CB3A-1.5Ca salt | mouse | a | >2000 |
| | | b | >500 |
| | rat | a | >2000 |
| | | b | >500 |
| CB3A-Al salt | mouse | a | >2000 |
| | | b | >500 |
| | rat | a | >2000 |
| | | b | >500 |
| CK3A-3K salt | mouse | a | >2000 |
| | | b | >500 |
| | rat | a | >2000 |
| | | b | >500 |
| CK3A-3Na salt | mouse | a | >2000 |
| | | b | >500 |
| | rat | a | >2000 |
| | | b | >500 |
| CK3A-1.5Ca salt | mouse | a | >2000 |
| | | b | >500 |
| | rat | a | >2000 |
| | | b | >500 |
| CK3A-Al salt | mouse | a | >2000 |
| | | b | >500 |
| | rat | a | >2000 |
| | | b | >500 |
| CB3A | mouse | a | >2000 |
| | | b | >500 |
| | rat | a | >2000 |
| | | b | >500 |
| CK3A | mouse | a | >2000 |
| | | b | >500 |
| | rat | a | >2000 |
| | | b | >500 | note:
a ... per os (oral administration)
b ... intraperitoneal injection

Among the above-mentioned metal salts, calcium salts of CB3A and CK3A showed less toxicitic effect.

(3) Stability

One gram each of CB3A, CK3A and various metal salts thereof was placed in a beaker and the beaker was allowed to stand for 5 weeks in a constant temperature and humidity bath controlled at a temperature of 45° C. and a humidity of 80%. After 5 weeks, a remaining rate of the compound was analyzed quantitatively with a high performance liquid chromatography "Tri rotar" manufactured by Nippon Bunko K. K. (Japan). The results are shown in Table 3.

It is clear that the metal salts of organic phosphate according to the present invention maintain higher remaining rate and show much higher stability than CB3A and CK3A.

TABLE 3

| Compound | Remaining rate (%) |
|---|---|
| CB3A-3Na salt | 82 |
| CB3A-2Na salt | 78 |
| CB3A-1Na salt | 74 |
| CB3A-1.5Ca salt | 97 |
| CB3A-Al salt | 98 |
| CB3A methyl ester-2K salt | 84 |
| Ck3A 3K salt | 85 |
| CK3A 1.5Ca salt | 96 |
| CK3A-Al salt | 98 |
| CK3A methyl ester-2K salt | 83 |
| CB3A | 14 |

TABLE 3-continued

| Compound | Remaining rate (%) |
| --- | --- |
| CK3A | 13 | note:

Remaining rate (%) = $\frac{A_1}{A_0} \times 100$ $A_0$ = initial amount of the compound prior to standing in the constant temperature and humidity bath
$A_1$ = final amount of the compound after 5 weeks It is clear from the results shown in Tables 1, 2 and 3, the metal salts of organic phosphate according to the present invention are much more effective than CB3A and CK3A when given in various administrations, for example, intravenously or orally.

When the metal salt of organic phosphate according to the present invention is used for the treatment of hyperlipemia, the dose thereof varies depending on administration routes and times, but is preferably from 0.5 to 500 mg a day for adult, for example from 2 to 20 mg in case of mild patient and from 20 to 300 mg in case of serious patient. By analogy of other lipid-lowering agents such as Clofibrate or Simfibrate, the metal salt of organic phosphate according to the present invention is treated in any conventional manner to provide any administration forms.

Accordingly, the present invention includes a pharmacentical composition suitable for a human drug which contains at least one of metal salts of organic phosphate represented by the above mentioned formula (1).

The composition together with a pharmeceutical carrier or excipient is provided in a conventional manner. It is preferable that the composition is provided in a form suitable for the absorption from gastrointestinal tract.

A tablet or capsule for oral administration is a form of unit dose and may contain a binder such as syrup, gum arabi, gelatin, sorbit, tragacanth and polyvinyl pyrrolidone; an excipient or vehicle such as lactose, sugar, corn starch, calcium phosphate, sorbit and glycine; a lubricant such as magnesium stearate, talc, polyethylene glycol and silica; a disintegrator such as potato starch; or a pharmaceutically acceptable wetting agent, for example a conventional excipient such as sodium lauryl sulfate. The tablet may have a coating which is provided in a manner conventional in the art.

A liquid formulation for oral administration is based on an aqueous or oily dispersion, solution, syrup, elixir or the like. A dry formulation may be dissolved in water or other suitable vehicles before use. The liquid formulation may contain conventionally used additives. For example a suspending agent such as sorbit syrup, methyl cellulose, glucose syrup, gelatin, hydroxyethyl cellulose, carboxymethyl cellulose, aluminum stearate gel or hydrogenated edible fats: an emulsifier such as lecithin, sorbitan monooleate and gum arabi; a nonaqueous vehicle such as almond oil, fractionated coconut oil, oily ester, propylene glycol and ethyl alcohol; and an antiseptic such as methyl p-hydroxybenzoate, propyl p-hydroxybenzoate and sorbic acid An injection composition is provided in a unit dose ample. The injection composition together with an antiseptic may be provided in a large scale container. For multiple dose, the composition may be a form of suspension, solution or emulsion in oily or aqueous vehicle. It may contain additives such as suspending agent, stabilizing agent and/or dispersing agent.

These compositions can contain 0.1% or more, preferably from 10 to 60% of active substance, depending on modes of administration.

When the composition consists of a unit dose, it is preferable that each unit contains from 0.5 to 500 mg of active substance.

The present invention will be further described below referring to Referential Examples, Preparation Examples and Formulation Examples.

REFERENTIAL EXAMPLE 1

Preparation of CK3A and its methyl ester

To a pair of 500 ml Erlenmeyer flasks was added 100 ml each of culture medium containing 1% of glucose. 0.2% of peptone, 0.1% of meat extract, 0.1% of yeast extract, 0.3% of corn steep liquor and the balance of purified water. Circinella muscae IFO 4457 was innoculated in the culture medium and cultured under shaking at 25° C. for 2 days.

The culture solutions were respectively transferred to 5 l Erlenmeyer flasks containing 1 l of a culture medium of the same composition as above and cultured again under shaking at 25° C. for 3 days.

Thereafter 10 ml each of 5% aqueous solution of Monacolin K sodium salt was added to respective Erlenmeyer flasks and shaking culturing was further conducted at 25° C. for 5 days.

After culturing, the conversion reaction solution was filtered and the filtrate was adjusted to pH 3 with trifluoroacetic acid. After the pH-adjusted filtrate was extracted three times with 1 l of ethyl acetate, the extract was dried over anhydrous sodium sulfate, and then evaporated to dryness to obtain 2.01 g of the residue containing the conversion reaction products. After the residue was dissolved in 50 ml of 5% aqueous sodium bicarbonate solution, the aqueous extract was adjusted to pH 3 with 50% aqueous phosphoric acid and extracted with 50 ml of ethyl acetate. After the organic extract was dried over anhydrous sodium sulfate, it was evaporated to dryness to obtain 418 mg of the dried residue. After it was dissolved in 2 ml of methanol and incubated at 37° C. for 24 hours, the methanolic solution incubated was fractionated with a high performance liquid chromatography manufactured by Nippon Bunko K. K. (column: Fine SIL-C18 fractionation, mobile phase: acetonitrile/aqueous phosphoric acid (pH 2)=40/60) to obtain 25 mg of CK3A and 53 mg of CK3A methyl ester.

REFERENTIAL EXAMPLE 2

Preparation of CB3A and its methyl ester

Circinella muscae IFO 4457 was inoculated in a pair of 500 ml Erlenmeyer flasks containing 100 ml of the same culture medium as in Referential Example 1 and cultured under shaking at 25° C. for 2 days. The culture solutions were respectively transferred to 5 l Erlenmeyer flasks containing 1 l of the same culture medium as above and cultured again at 25° C. for 3 days. Thereafter sodium salt of ML-236B was added in such an amount that a final concentration thereof was controlled to 0.05% and culturing was conducted at 25° C. for 5 days. After culturing, the conversion reaction solution was filtered and the filtrate was adjusted to pH 3 with trifluoroacetic acid. The pH-adjusted filtrate was extracted three times with 1 l of ethyl acetate and the extract was dried over anhydrous sodium sulfate and then evaporated to dryness. The residue was dissolved in 50 ml of ethyl acetate and extracted with the same volume of 5% aqueous solution of sodium bicarbonate. After the aqueous extract was adjusted to pH 3 with 50% aqueous phosphoric acid, it was extracted with 50 ml of ethyl acetate. The organic extract was dried over anhydrous sodium sulfate and evaporated to dryness to obtain 346 mg of the residue. After it was dissolved in 2 ml of methanol and incubated at 37° C. for 24 hours, the methanolic solution incubated was fractionated with a high performance liquid chromatography manufactured by Nippon Bunko K. K. (column: Silica-C18, mobile phase: acetonitrile/aqueous phosphoric acid (pH 2)=40/60 to obtain 21 mg of CB3A and 45 mg of CB3A methyl ester.

REFERENTIAL EXAMPLE 3

Preparation of CB3A

Circinella muscae IFO 4457 was inoculated in a potato-sucrose agar and cultured at 25° C. for on week to form spores. A physiological table salt solution was added thereto and hyphas were removed with a glass filter to obtain a spore suspension (number of spores ca $10^6$/ml).

One hundred sixteen grams of κ-carrageenan was added under stirring to 3.1 l of a physiological table salt solution and sterilized in an autoclave. The resulting solution was mixed with 780 ml of the above mentioned spore suspension to obtain a carrageenan-spore mixture wherein spores were dispersed therein.

The carrageenan-spore mixture was added dropwise with an injector to an immoblizing liquid comprising an aqueous solution containing 0.2 mol/l of potassium chloride and a soy bean oil layer with a thickness of ca 1.5 cm provided thereon. After the globular immobilized gel formed was subjected to filtration and washed with an aqueous solution containing 0.2 mol/l of potassium chloride to obtain 4.0 kg of a spore-immobilized globular gel.

The spore-immobilized globular gel (4.0 kg) was added to 20 l of a "growth" culture medium containing 2 wt % of glucose, 0.6 wt % of corn steep liquor, 0.2 wt % of meat extract, 0.2 wt % of yeast extract and 0.2 wt % of polypeptone. The resulting mixture is aerobically cultured at 25° C. for 4 days to germinate spores and form hypha plexus uniformly in the gel.

The mixture was filtered to separate the immobilized globular gel, which was thereafter transferred to 20 l of a "conversion" culture medium composed of 500 μg/ml of sodium salt of ML-236B. 100 μg/ml of magnesium sulfate (heptahydrate), 15 μg/ml of iron sulfate, 10 μg/ml of manganese sulfate and 0.05 m mole/ml of potassium phosphate (pH 6.0). Aerobically culturing was conducted at 25° C. for 24 hours. The culture solution was filtered to separare 20 l of a filtrate (1st filtrate) from the immobilized globular gel. The recovered gel was mixed again with 20 l of the same culture medium as mentioned above and aerobically culturing was conducted at 25° C. for 24 hours. The second culture solution was filtered to separate 20 l of a filtrate (2nd filtrate) from the immobilized globular gel. The same aerobically culturing procedure as mentioned above was repeated additional three times to obtain 20 l each of three filtrates (3rd, 4th and 5th filtrates).

These filtrates were analyzed with a high performance liquid chromatography (column: Silica-C18) manufactured by Nippon Bunko K. K. to determine the conversion rate of ML-236B to CB3A. The results are as follows.

|  | Conversion rate |
| --- | --- |
| 1st filtrate | 95% |
| 2nd filtrate | 86% |
| 3rd filtrate | 77% |
| 4th filtrate | 64% |
| 5th filtrate | 58% |

After combined, the five filtrates were concentrated to a volume of 10 l with a reverse osmosis evaporator manufactured by Nippon Abuko K. K. (Japan). and then acidified to pH 3 by addition of 50% aqueous phosphoric acid. The concentrate was extracted three times with 5 l of ethyl acetate, and the ethyl acetate extract was dried over anhydrous sodium sulfate and evaporated under reduced pressure to obtain a dried residue. The dried residue was dissolved in 1 l of 5% aqueous sodium bicarbonate and washed with 1 l of ethyl acetate. Thereafter the aqueous layer was acidified to pH 3 by addition of 50% aqueous phosphoric acid and extracted three times with 1 l of ethyl acetate. The ethyl acetate layer was dried over anhydrous sodium sulfate and evaporated to dryness to obtain 53.1 g of a dried residue.

The dried residue was passed through a silica gel choromatography column (silica gel: Wako gel C-200 2.0 kg, solvent: hexane/acetone) to collect fractions of hexane/acetone (60/40-40/60), which were thereafter evaporated to dryness to finally obtain 33.2 g of CB3A.

REFERENTIAL EXAMPLE 4

Preparation of CK3A

The procedure of Referential Example 3 was repeated except that Monacolin K was used instead of ML-236B. The yield of CK3A from Monacolin K was 31.7 g.

REFERENTIAL EXAMPLE 5

Preparation of CB3A

The procedure of Referential Example 3 was repeated except that *Absidia cylindrospora* IFO 4000 was used in place of *Circinella muscae* IFO 4457. The yield of CB3A from ML-236B was 29.3 g.

REFERENTIAL EXAMPLE 6

Preparation of CK3A

The procedure of Referential Example 4 was repeated except that *Absidia cylindrospora* IFO 4000 was used instead of *Circinella muscae* IFO 4457. The yield of CK3A from Monacolin K was 30.1 g.

REFERENTIAL EXAMPLE 7

Preparation of CB3A methyl ester

Two grams of CB3A prepared in Referential Example 5 was dissolved in 40 ml of methanol. One ml of 85% aqueous phosphoric acid was added thereto and the resulting mixture was incubated at 40° for 24 hours. The methanolic solution incubated was fractioned with a high performance liquid chromatography manufactured by Nippon Bunko K. K. (column: Silica-C18, mobile phase: acetonitrile/aqueous phosphoric acid (pH 2)=50/50) to obtain 1.8 grams of CB3A methyl ester.

REFERENTIAL EXAMPLE 8

Preparation of CK3A methyl ester

The procedure of Referential Example 7 was repeated except that CB3A was used instead of CK3A prepared in Referential Example 4. The yield of CK3A methyl ester from CK3A was 1.7 g.

PREPARATION EXAMPLE 1

Trisodium salt of CB3A (CB3A-3Na salt)

Ten grams of CB3A prepared in Referential Example 3 was dissolved in 100 ml of water. 61.5 ml of IN-NaOH solution was added thereto and the resulting mixture was stirred well at room temperature. The aqueous solution was then freeze-dried to obtain 11.0 g of trisodium salt of CB3A [$R_1=R_2=R_3=Na$, $R_4=H$ in the formula (1)].

The ultraviolet absorption spectra (aqueous solution) are as follows.

| λ max (nm) | $\epsilon_{1\ cm}^{1\%}$ |
|---|---|
| 229 | 349 |
| 237 | 397 |
| 245 | 264 |

The obtained trisodium salt of CB3A has excellent water solubility and stability.

PREPARATION EXAMPLE 2

Tripotassium salt of CB3A (CB3A-3K salt)

Ten grams of CB3A prepared in Referential Example 3 was dissolved in 100 ml of water. 61.5 ml of IN-KOH solution was added thereto and the resulting solution was stirred well at room temperature. The aqueous solution was then freeze-dried to obtain 11.9 g of tripostassium salt of CB3A [$R_1=R_2=R_3=K$, $R_4$ in the formula (1)].

The ultraviolet absorption spectra (aqueous solution) are as follows.

| λ max (nm) | $\epsilon_{1\ cm}^{1\%}$ |
|---|---|
| 229 | 320 |
| 237 | 366 |
| 245 | 244 |

The obtained tripotassium salt of CB3A has excellent water solubility and stability.

PREPARATION EXAMPLE 3

Dipotassium salt of CB3A CB3A-2K salt)

Ten grams of CB3A prepared in Referential Example 3 was dissolved in 100 ml of water. 41.0 ml of IN-KOH solution was added thereto and the resulting solution was stirred well at room temperature. The aqueous solution was freeze-dried to obtain 10.7 g of dipotassium salt of CB3A.

The ultraviolet absorption spectra thereof are as follows.

| λ max (nm) | $\epsilon_{1\ cm}^{1\%}$ |
|---|---|
| 229 | 343 |
| 237 | 390 |
| 245 | 259 |

The obtained dipotassium salt of CB3A has excellent water solubility and stability.

Since the acidity ($pKa_1=2.2$, $pKa_2=5.0$) of the phosphoric acid group in CB3A molecule is stronger than that ($pKa_3=7.1$) of the carboxylic acid group in CB3A molecule, the dipotassium salt of CB3A is the compound of the formula (1) wherein $R_1=H$, $R_2=R_3=K$, and $R_4=H$.

PREPARATION EXAMPLE 4

Monopotassium salt of CB3A (CB3A-K salt)

Ten grams of CB3A obtained in Referential Example 5 was dissolved in 100 ml of water. Thereafter, 20.5 ml of IN-KOH solution was added thereto and the resulting solution is stirred well at room temperature. The aqueous solution was then freeze-dried to obtain 10.2 g of monopotassium salt of CB3A [$R_1=R_2=H$, $R_3=K$, $R_4=H$].

The ultraviolet spectra thereof are as follows.

| λ max (nm) | $\epsilon_{1\ cm}^{1\%}$ |
|---|---|
| 230 | 366 |
| 237 | 419 |
| 246 | 280 |

The obtained monopotassium salt of CB3A has excellent water solubility and stability.

PREPARATION EXAMPLE 5

Sesquicalcium salt of CB3A (CB3A-1.5Ca salt)

The trisodium salt (1.2 g) of CB3A obtained in Preparation Example 1 was dissolved in 80 ml of water. 20ml of 10% $CaCl_2\ 2H_2O$ solution was slowly added thereto and the resulting mixture was stirred thoroughly and then allowed to stand overnight. The resulting white precipitate was collected by centrifugation. The collected precipitate was suspended in 30 ml of water and recollected by centrifugation. This operation was repeated three times. The precipitate finally obtained was suspended in 5 ml of water and freeze-dried to obtaine 1.1 g of sesquicalcium salt of CB3A (dihydrate) [$R_1=R_2=R_3=Ca$, $R_4=H$ in the formula (1)]

| (1) Ultraviolet absorption spectra (aqueous solution) | |
|---|---|
| λ max (nm) | $\epsilon_{1\ cm}^{1\%}$ |
| 229 | 328 |
| 237 | 379 |
| 245 | 250 |

| (2) Elementary analysis (%) | | | | |
|---|---|---|---|---|
| | C | H | P | Ca |
| Calculated | 47.50 | 6.58 | 5.32 | 10.34 |
| Found | 47.23 | 6.59 | 5.33 | 10.17 |

The obtained sesquicalcium salt of CB3A has no hygroscopic property and shows particularly excellent stability.

PREPARATION EXAMPLE 6

Sesquibarium salt of CB3A (CB3A-1.5Ba salt)

The trisodium salt (1.2 g) of CB3A obtained in Preparation Example 1 was dissolved in 80 ml of water. 20ml of 25% $BaCl_2\ 2H_2O$ solution was slowly added thereto and the resulting mixture was stirred thoroughly and then allowed to stand overnight. The resulting white precipitate was collected by centrifugation. The collected precipitate was suspended in 30 ml of water and re-collected by centrifugation. This operation was repeated three times. The precipitate finally obtained was suspended in 5 ml of water and freeze-dried to obtain 1.2 g of sesquibarium salt of CB3A [$R_1=R_2=R_3=Ba$, $R_4=H$ in the formula (1)]

(1) Ultraviolet absorption spectra (aqueous solution)

| λ max (nm) | $\epsilon_{1\ cm}^{1\%}$ |
| --- | --- |
| 229 | 258 |
| 237 | 299 |
| 245 | 197 |

(2) Elementary analysis (%)

| | C | H | P | Ba |
| --- | --- | --- | --- | --- |
| Calculated | 39.95 | 4.96 | 4.48 | 29.79 |
| Found | 40.11 | 4.92 | 4.56 | 29.62 |

The obtained sesquibarium salt of CB3A has no hygroscopic property and shows particularly excellent stability.

PREPARATION EXAMPLE 7

Aluminum salt of CB3A (CB3A-Al salt)

The sodium salt (1.2 g) of CB3A obtained in Preparation Example 1 was dissolved in 80 ml of water. 20 ml of 5% $AlCl_3\ 6H_2O$ solution was slowly added thereto and the resulting mixture was stirred thoroughly and then allowed to stand overnight. The resulting white precipitate was collected by centrifugation. The collected precipitate was suspended in 30 ml of water and recollected by centrifugation. This operation was repeated three times. The precipitate finally obtained was suspended in 5 ml of water and freeze-dried to obtain 1.1 g of aluminum salt of CB3A (tetrahydrate) [$R_1=R_2=R_3=Al$, $R_4=H$ in the formula (1)].

(1) Ultraviolet absorption spectra (MeOH solution)

| λ max (nm) | $\epsilon_{1\ cm}^{1\%}$ |
| --- | --- |
| 229 | 329 |
| 237 | 377 |
| 245 | 253 |

(2) Elementary analysis (%)

| | C | H | P | Al |
| --- | --- | --- | --- | --- |
| Calculated | 47.26 | 7.24 | 5.30 | 4.62 |
| Found | 47.85 | 7.19 | 5.34 | 4.51 |

The obtained aluminum salt of CB3A had no hydroscopic property and shows particularly excellent stability.

PREPARATION EXAMPLE 8

Dipotassium salt of CB3A methyl ester(CB3A methyl ester-2K salt)

CB3A methyl ester (1.0 g) prepared in Referential Example 7 was dissolved in 10 ml of water. 3.98 ml of 1N-KOH solution was added thereto and the resulting mixture was stirred well at room temperature. The aqueous solution was freeze-dried to obtain 1.1 g of dipotassium salt of CB3A methyl ester [$R_1=CH_3$, $R_2=R_3=K$, $R_4=H$].

The ultraviolet absorption spectra (aqueous solution) are as follows.

| λ max (nm) | $\epsilon_{1\ cm}^{1\%}$ |
| --- | --- |
| 229 | 333 |
| 237 | 381 |
| 245 | 254 |

The obtained dipotassium salt of CB3A methyl ester has excellent water solubility and stability.

PREPARATION EXAMPLE 9

Calcium salt of CB3A methyl ester (CB3A methyl ester-Ca salt)

The dipotassium salt (0.5 g) of CB3A methyl ester obtained in Preparation Example 8 was dissolved in 40 ml of water. 6 ml of 10% $CaCl_2\ 2H_2O$ solution was slowly added thereto and the resulting mixture was stirred thoroughly and then allowed to stand overnight. The resulting precipitate was collected by filtration with a glass filter (No.4), washed well with water and vacuum dried to obtain 0.4 g of calcium salt of CB3A methyl ester [$R_1=CH_3$, $R_2=R_3=Ca$, $R_4=H$ in the formula (1)].

The ultraviolet absorption spectra (aqueous solution) are as follows.

| λ max (nm) | $\epsilon_{1\ cm}^{1\%}$ |
| --- | --- |
| 229 | 331 |
| 237 | 383 |
| 245 | 253 |

The obtained calcium salt of CB3A methyl ester has no hygroscopic property and shows particularly excellent stability.

PREPARATION EXAMPLE 8

Trisodium salt of CK3A (CK3A-3Na salt)

Three grams of CK3A prepared in Referential Example 4 was dissolved in 30 ml of water. 18.0 ml of 1N-NaOH solution was added thereto and the resulting mixture was stirred well at room temperature. The aqueous solution was freeze-dried to obtain 3.4 g of trisodium salt of CK3A [$R_1=R_2=R_3=Na$, $R_4=CH_3$ in the formula (1)].

The ultraviolet absorption spectra are as follows.

| λ max (nm) | $\epsilon_{1\ cm}^{1\%}$ |
| --- | --- |
| 230 | 340 |
| 237 | 387 |
| 246 | 260 |

The obtained trisodium salt of CK3A has excellent water solubility and stability.

PREPARATION EXAMPLE 9

Tripotassium salt of CK3A (CK3A-3K salt)

One gram of CK3A prepared in Referential Example 4 was dissolved in 20 ml of water. 6.0 ml of 1N-KOH solution was added thereto and the resulting mixture was stirred well at room temperature. The aqueous solution was freeze-dried to obtain 1.2 g of tripotassium salt of CK3A [$R_1=R_2=R_3=K$, $R_4=CH_3$ in the formula (1)].

The ultra violet absorption spectra (aqueous solution) are as follows.

| λ max (nm) | $\epsilon_{1\ cm}^{1\%}$ |
| --- | --- |
| 230 | 311 |
| 237 | 355 |
| 246 | 237 |

The obtained tripotassium salt of CK3A has excellent water solubility and stability

PREPARATION EXAMPLE 10

Sesquicalcium salt of CK3A (CK3A-1.5Ca salt)

The trisodium salt (0.5 g) of CK3A prepared in Preparation Example 10 was treated in the same manner as in Preparation Example 5 to obtain 0.4 g of sesquicalcium salt of CK3A (dihydrate) [$R_1=R_2=R_3=Ca$, $R_4=CH_3$ in the formula (1)].

The ultraviolet absorption spectra (aqueous solution) are as follows.

| λ max (nm) | $\epsilon_{1\ cm}^{1\%}$ |
| --- | --- |
| 230 | 320 |
| 237 | 369 |
| 246 | 243 |

The sesquicalcium salt of CK3A obtained has no hygroscopic property and shows particularly excellent stability.

PREPARATION EXAMPLE 11

Sesquibarium salt of CK3A (CK3A-1.5Ba salt)

The trisodium salt (0.5 g) of CK3A prepared in Preparation Example 10 was treated in the same manner as in Preparation Example 6 to obtain 0.4 g of sesquibarium salt of CK3A [$R_1=R_2=R_3=Ba$, $R_4=CH_3$ in the formula (1)].

The ultraviolet absorption spectra (aqueous solution) are as follows.

| λ max (nm) | $\epsilon_{1\ cm}^{1\%}$ |
| --- | --- |
| 230 | 244 |
| 237 | 281 |
| 246 | 185 |

The obtained sesquibarium salt of CK3A has no hygroscopic property and shows particularly excellent stability.

PREPARATION EXAMPLE 12 cAluminum salt of CK3A (CK3A-Al salt)

The trisodium salt (0.5 g) of CK3A prepared in Preparation Example 10 was treated in the same manner as in Preparation Example 7 to obtain 0.4 g of aluminum salt of CK3A (hydrate) [$R_1=R_2=R_3=Al$, $R_4=CH_3$ in the formula (1)].

The ultraviolet absorption spectra (methanolic solution) are as follows.

| λ max (nm) | $\epsilon_{1\ cm}^{1\%}$ |
| --- | --- |
| 230 | 319 |
| 237 | 368 |
| 246 | 242 |

The obtained aluminum salt of CK3A has no hygroscopic property and shows particularly excellent stability.

PREPARATION EXAMPLE 13

Dipotassium salt of CK3A methyl ester (CK3A methyl ester-2K salt)

One gram of CK3A methyl ester prepared in Referential Example 8 was dissolved in 10 ml of water. 3.88 ml of 1N-KOH solution was added thereto and the resulting mixture was stirred well at room temperature. The aqueous solution was freeze-dried to obtain 1.1 g of dipotassium salt of CK3A methyl ester [$R_1=CH_3$, $R_2=R_3=K$, $R_4=CH_3$ in the formula (1)].

The ultraviolet absorption spectra (aqueous solution) are as follows.

| λ max (nm) | $\epsilon_{1\ cm}^{1\%}$ |
| --- | --- |
| 230 | 326 |
| 237 | 371 |
| 246 | 249 |

The obtained dipotassium salt of CK3A methyl ester has excellent water solubility and stability.

PREPARATION EXAMPLE 14

Calcium salt of CK3A methyl ester (CK3A methyl ester-Ca salt)

The dipotassium salt (0.5 g) of CK3A methyl ester prepared in Preparation Example 15 was dissolved in 40 ml of water. 6 ml of 10% aqueous $CaCl_2\ 2H_2O$ solution was slowly added thereto and the resulting mixture was stirred thoroughly and then allowed to stand overnight. The resulting precipitate was collected by filtration with a glass filter (No.4), washed well with water and vacuum dried to obtain 0.4 g of calcium salt of CK3A methyl ester [$R_1=CH_3$, $R_2=R_3=Ca$, $R_4=CH_3$ in the formula (1)].

The ultraviolet absorption spectra (aqueous solution) are as follows.

| λ max (nm) | $\epsilon_{1\ cm}^{1\%}$ |
| --- | --- |
| 230 | 322 |
| 237 | 373 |
| 246 | 245 |

The obtained calcium salt of CK3A methyl ester has no hygroscopic property and shows particularly excellent stability.

Hereunder are shown two examples wherein pharmaceutical formulations are prepared using the compound having the formula (1).

FORMULATION EXAMPLE 1

Capsular agent for oral administration sesquicalcium salt of CB3A: 250 mg
lactose: 75 mg
calcium stearate: 15 mg
total: 340 mg.

The powder components were mixed and passed through a screen of 60 meshes. The powder mixture passed through the screen was added into a No.1 gelatine capsule to obtain a capsular agent for oral administration.

FORMULATION EXAMPLE 2

Injection agent

The sterilized tripotassium salt (250 mg) of CK3A was sterilely distributed in a vial, sterilely freeze-dried and sealed. Prior to use, 2 ml of a physiological salt solution was added thereto to obtain an injection agent.

What is claimed is:

1. A metal salt of organic phosphate represented by the general formula (1):

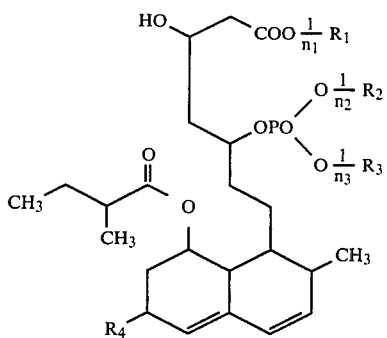

Wherein $R_1$, $R_2$ and $R_3$ are selected from the group consisting of hydrogen atom, alkyl group, alkali metal, alkaline earth metal, aluminum, iron, zinc, copper, nickel and cobalt, at least on of $R_1$, $R_2$ and $R_3$ being a metal; $n_1$, $n_2$ and $n_3$ are valences of $R_1$, $R_2$ and $R_3$, respectively; $R_4$ is hydrogen atom or methyl group; provided that there is excluded the case where $R_1$ is hydrogen or methyl group, and $R_2$ and $R_3$ are hydrogen atom.

2. A metal salt of organic phosphate according to claim 1, wherein $R_1$, $R_2$ and $R_3$ are selected from the group consisting of hydrogen atom, alkyl group, alkali metal, alkaline earth metal and aluminum.

3. An antihyperlipemic composition comprising an antihyperlipemic-effective amount of a metal salt of organic phosphate represented by the general formula (1):

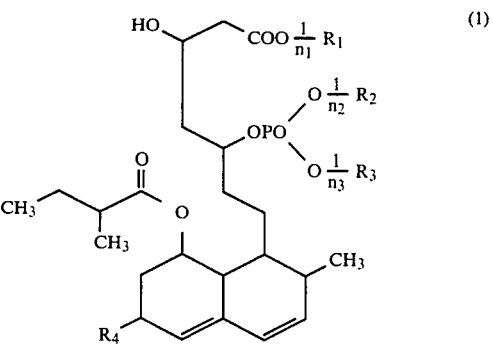

wherein $R_1$, $R_2$ and $R_3$ are selected from the group consisting of hydrogen atom, alkyl group, alkali metal, alkaline earth metal, aluminum, iron, zinc, copper, nickel and cobalt, at least one of $R_1$, $R_2$ and $R_3$ being a metal; $n_1$, $n_2$ and $n_3$ are valences of $R_1$, $R_2$ and $R_3$, respective; $R_4$ is hydrogen atom or methyl group; provided that there is excluded the case where $R_1$ is hydrogen or methyl group, and $R_2$ and $R_3$ are hydrogen atom in admixture with a pharmaceutically acceptable excipient.

4. An antihyperlipemic composition according to claim 3, wherein $R_1$, $R_2$ and $R_3$ are selected from the group consisting of hydrogen atom, alkyl group, alkali metal, alkaline earth metal and aluminum.

* * * * *